United States Patent [19]
Williams et al.

[11] Patent Number: 5,104,508
[45] Date of Patent: Apr. 14, 1992

[54] ANALYSIS OF CARBOHYDRATES

[75] Inventors: Gwynfor R. Williams, Castletown, Isle of Man; Peter Jackson, Fulbourn, Great Britain

[73] Assignee: Astroscan Ltd., Douglas, Isle of Man

[21] Appl. No.: 317,480

[22] PCT Filed: Jun. 20, 1988

[86] PCT No.: PCT/GB88/00472
§ 371 Date: Feb. 14, 1989
§ 102(e) Date: Feb. 14, 1989

[87] PCT Pub. No.: WO88/10422
PCT Pub. Date: Dec. 29, 1988

[30] Foreign Application Priority Data

Jun. 18, 1987 [GB] United Kingdom ............... 8714270

[51] Int. Cl.$^5$ ............... B01D 61/42; C25D 13/00; C01N 21/00
[52] U.S. Cl. ............... 204/182.8; 204/299 R; 356/344
[58] Field of Search ............... 204/180.1, 182.8; 356/344

[56]  References Cited
FOREIGN PATENT DOCUMENTS
2175690A 12/1986 United Kingdom ............... 356/344

OTHER PUBLICATIONS

Analytical Biochemistry 115, pp. 170-176 (1981) (Poretz et al.).
Analytical Biochemistry 97, pp. 438-449 (1979) (Weitzman et al.).
J. Biochem., vol. 85, No. 4, pp. 989-994 (1979) (Hase et al.).
"Heterogeneity of Lipopolysaccharides, Analysis of Polysaccharide Chain Lengths by Sodium Dodecylsulfate-Polyacrylamide Gel Electrophoresis", Barbara Jann, Konrad Reske, and Klaus Jann, Eur. J. Biochem., vol. 60, pp. 239-246 (1975).

*Primary Examiner*—John F. Niebling
*Assistant Examiner*—Caroline Koestner
*Attorney, Agent, or Firm*—Lee, Mann, Smith, McWilliams & Sweeney

[57]  ABSTRACT

A carbohydrate structure, possibly in the form of or derived from a glycoprotein or glycolipid, is analyzed by decomposing the structure into various constituent fragments, separating the fragments and viewing light from the separated fragments using a charge coupled device (CCD). Carbohydrate units can be distinguished or separated by gel electrophoresis, e.g. using a relatively dense polyacrylamide gel run using a stacking buffer system. The two aspects can be used separately or in combination.

13 Claims, 4 Drawing Sheets

TRACKS  24 23 22 21 20 19 18 17 16 15 14 13

TRACKS  12 11 10 9 8 7 6 5 4 3 2 1

ANALYSIS OF CARBOHYDRATES

FIELD OF THE INVENTION

This invention relates to analysis of carbohydrates.

BACKGROUND TO THE INVENTION

A large number of different carbohydrates exist, including many compounds of importance in biological processes. Carbohydrate structures can occur alone, but sometimes also occur in association with biomolecules such as lipids (glycolipids, glycosphingolipids), proteins (glycoproteins, proteoglycans), or other molecular structures. Carbohydrates are made up of a variety of different monosaccharide units or building blocks, which may occur along, e.g. as glucose or fructose, or which may be linked by a range of different glycosidic bonds to form larger molecules such as disaccharides, e.g. lactose and sucrose, oligosaccharides and polysaccharides, e.g. cellulose and starch. Larger units may be linear or they may have a branched structure, e.g. as shown in FIG. 1, where Mn represents monosaccharide type "n".

Given two monosaccharide units (say M1 and M2) linked in a particular way it is often possible to find reagents or groups of reagents (such as the enzymes known as glycosidases which cleave glycosidic bonds between monosaccharide units) which will selectively cleave the bond between M1 and M2 or between a monosaccharide and the molecular structure to which the monosaccharide is attached.

Given a suitable set of reagents e.g. enzymes, it is possible to cleave a carbohydrate structure in many possible ways, and to obtain a collection of different fragments which can be analysed by various separation methods such as by chromatography. From a knowledge of the resulting fragments it is possible to make various deductions concerning the structure of the original carbohydrate. This type of approach is described in, e.g., the paper by Tomiya et al. in Analytical Biochemistry, 163, 484–499 (1987).

However there are limitations to the known techniques, and the present invention aims to provide improved methods, and apparatus.

SUMMARY OF THE INVENTION

According to one aspect of the present invention there is provided a method of analysing a carbohydrate, comprising decomposing a carbohydrate structure into various constituent fragments, separating the fragments, and viewing light from the separated fragments using a charge coupled device (CCD).

In a further aspect the present invention provides apparatus for analysing a carbohydrate, comprising means for decomposing a carbohydrate structure into various constituent fragments, means for separating the fragments, and a CCD for detecting a pattern of light from the separated fragments.

Use of a CCD enables results to be analysed more conveniently and potentially with greater sensitivity than has hitherto been possible.

It is preferred to use a cooled 2-D CCD, operating in slow scan readout. One example of a suitable CCD system is the CCD 2000 Imaging System produced by Astromed Limited, Cambridge, United Kingdom. The CCD is preferably cooled to at least as low as $-25°$ C., with sensitivity being significantly increased by further cooling down as far as $-160°$ C. Typical operation temperatures are in the range $-40°$ C. to $-120°$ C.

Prior to viewing the separated fragments, some sort of treatment or processing may be required, either before or after separation, in order to make the fragments more conducive to visualisation.

For example, the structure prior to treatment of the resulting fragments may be labelled in known manner with a detectable labelling reagent, e.g. a radioactive, fluorescent or luminescent compound. As a further possibility, treatment may be effected with a reagent or reagents to produce a detectable colourimetric change.

The labeling reagent may be attached to sites on the carbohydrate units, after release if necessary from an attached biomolecule. Alternatively, the biomolecule may be modified in known way to enable incorporation of a suitable labeling reagent.

The carbohydrate structure may be decomposed by known chemical techniques, e.g. as disclosed in the paper referred to above.

The collection of fragments may be separated by any convenient technique including chromatographic techniques silica, aluminium oxide or other comparable absorbants.

Hitherto only certain separation techniques have been used for carbohydrates fragments, including thin layer chromatography (TLC), high performance liquid chromatography (HPLC), and gas-liquid chromatography. These techniques separate on the basis of differential absorption, and so are well suited to carbohydrate fragments which can be of relatively low and similar molecular weight and charge. Another separation technique, gel electrophoresis, separates on the basis of differential mobility in an electric field (which depends on the size, shape and charge of units) and is widely used for separation of protein and DNA fragments, which are of relatively high molecular weight, but has not hitherto been used or considered suitable for distinguishing carbohydrate fragments.

It has now been found, contrary to expections, that it is possible to distinguish or separate carbohydrate units by gel electrophoresis under appropriate conditions.

Hence in a further aspect the present invention provides a method of distinguishing carbohydrate units, comprising applying carbohydrate units to an electrophoretic gel, and running the gel to cause differential migration of different units.

The gel preferably comprises a relatively dense polyacrylamide gel, having a concentration in the range 15% to 60%, preferably 25% to 40%, although in some cases it may be possible or preferable to use gels of lower concentration.

The gel may be either of uniform concentration, or in the form of a gradient gel.

The gel is preferably cross linked, e.g. with N,N' methylenebisacrylamide.

For good sensitivity the gel is preferably run using a stacking buffer system (also known as moving boundary electrophoresis, multizone electrophoresis and other names), using techniques known for working with protein and DNA fragments, e.g. as described in the book "Gel electrophoresis of proteins: a practical approach" edited by B D Hames and D Rickwood, published by IRL Press.

The carbohydrate units can be labelled in known manner as described above, e.g. by being tagged with a fluorescent or coloured marker, preferably prior to running the gel. After running the gel the labelled carbohydrate units may be visible with the naked eye in some cases, although better resolution and sensitivity will generally be obtained by imaging with a CCD, as described above. Further, a CCD can be used to view the gel while it is being run.

The use of electrophoresis gels has certain advantages as compared with chromatographic techniques:

1. The gel materials are generally clear, improving visualisation possibilities.

2. The gel materials are generally of low fluorescence, which is of advantage when using fluorescent markers.

3. Potentially higher resolution is possible than can be achieved with techniques such as TLC or HPLC.

In a preferred aspect the present invention provides a method of distinguishing carbohydrate units, comprising labelling the carbohydrate units with a fluorescent marker, applying the marked units to an electrophoretic gel comprising polyacrylamide having a concentration in the range of 15 to 60%, running the gel to cause differential migration of different units, and viewing light from different units using a CCD.

The invention is applicable to sequencing of a wide range of carbohydrate structures, including glycoproteins, glycolipids and glycosphingolipids.

When practicing the method of analysis of the invention a sample of the given carbohydrate structure is obtained and preferably divided into a number of portions. Each portion is treated separately with a different reagent (such as an enzyme) or group of different reagents which are capable of selectively cleaving particular bonds of a carbohydrate structure, either together or in sequence. The treatment proceeds for a calculated, appropriate amount of time and then is stopped by some termination procedure.

Prior to commencement of the above treatment, during the treatment, or at the end of the treatment the carbohydrate structure and its fragments may be derivatised or labelled so as to be visualisable, e.g. with radioactive, fluorescent, luminescent or coloured compounds. Suitable materials for this purpose are well known to those skilled in the field. For example, certain fluorescent labels including 7-amino-4-methylcoumarin are discussed in a paper by Prakash et al. in Analytical Biochemistry, 128, 41–46 (1983).

For each portion, the carbohydrate whole and fragments are then separated into the constituent parts using an appropriate technique, such as thin layer chromatography, gel electrophoresis etc.

After the initial separation, it is possible for samples to be physically removed from, say, a gel or chromatographic plate for further treatment and analysis if required, to yield further information.

By viewing the resulting chromatographs, electrophoretograms or other arrays with a CCD, a considerable amount of information on the molecular structure of the fragments can be obtained and conclusions drawn on the consitution and sequence of the original carbohydrate structure under consideration.

The invention will now be further described by way of illustration in the following Examples and by reference to the accompanying drawings, in which.

DESCRIPTION OF PREFERRED EMBODIMENT

Figure 2:
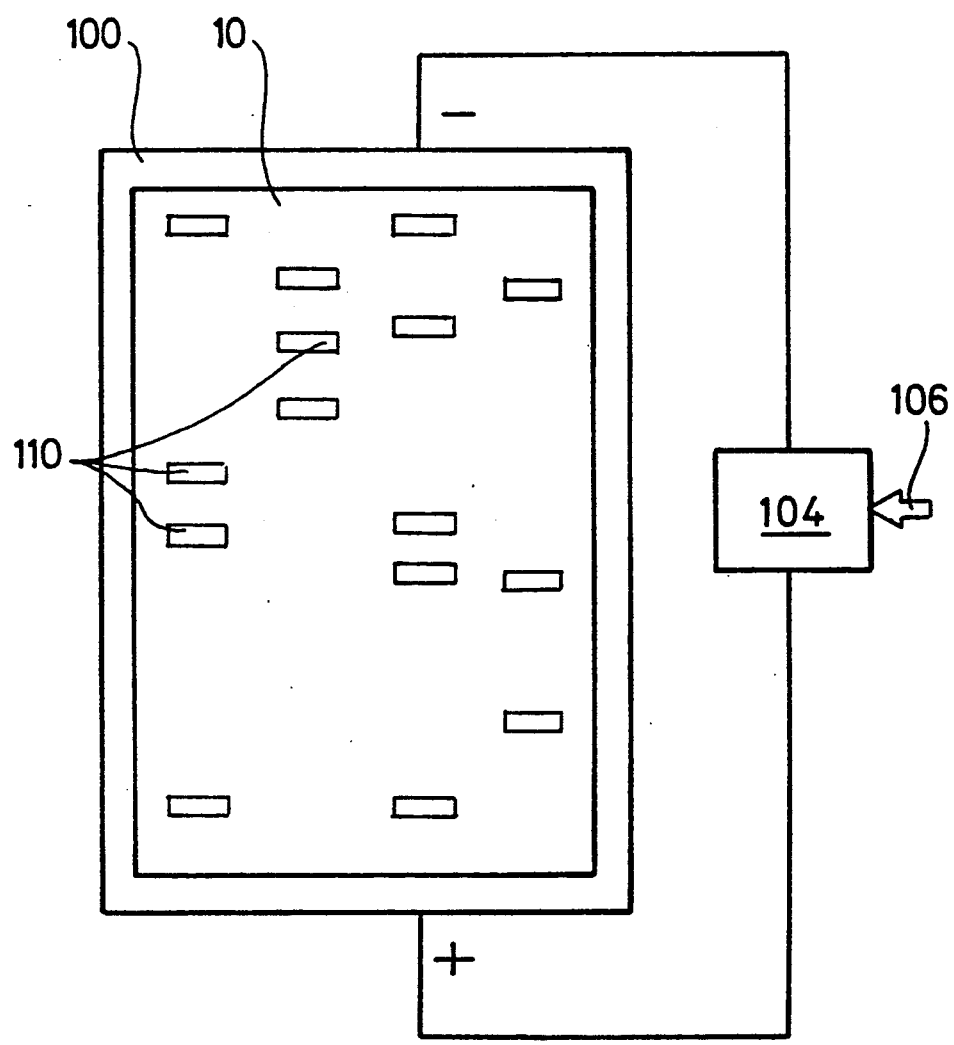
FIG. 2 illustrates schematically gel electrophoresis separation apparatus.
Figure 3:
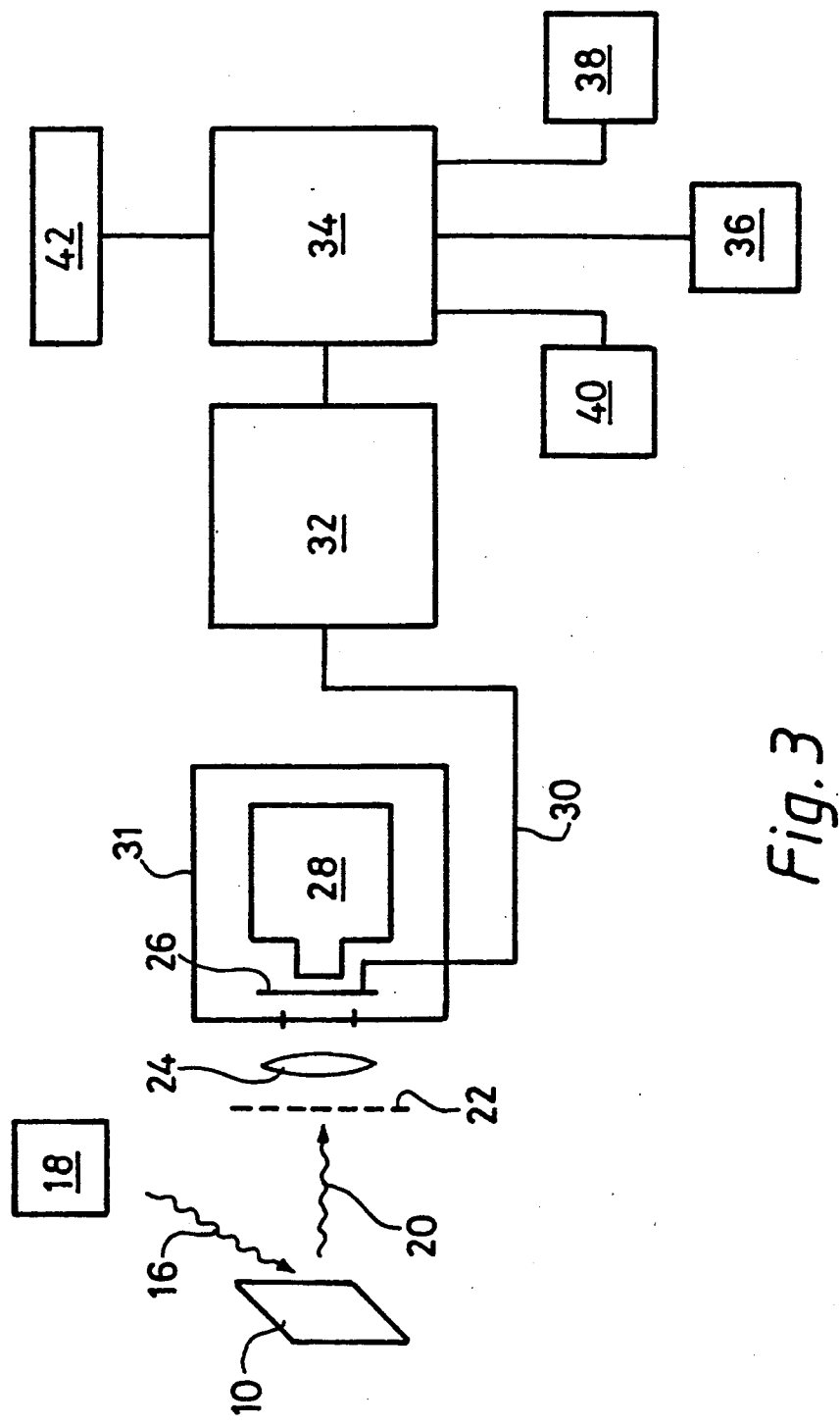
FIG. 3 illustrates schematically a CCD imaging system.

FIGS. 2 and 3 illustrate one embodiment of apparatus for distinguishing e.g. separating by gel electrophoresis carboydrate units and viewing the results with a CCD. Such apparatus can be used, for example, in a method of carbohydrate anaylysis of the invention, in which a carbohydrate structure is decomposed into fragments, e.g. by treatment with glycosidases, and the resulting fragments separated by gel electrophoresis and viewed with a CCD.

The electrophoresis apparatus of FIG. 2 comprises a tray-like container 100 containing an electrophoretic gel 10 of relatively dense e.g. 40% polyacrylamide. A voltage source 104 is employed to establish a controlled electric field across the gel, in the direction of the length of the tray, as indicated by the positive and negative signs. In the present case, the voltage source may itself be connected, via cable 106, to a computer forming part of the analysis apparatus of FIG. 3, so that the electrophoresis process is controllable in accordance with the requirements of the method of analysis.

The gel is used for separating or distinguishing carbohydrate units, which are preferably treated prior to application to the gel with fluorescent marking material, e.g. using conventional techniques such as disclosed in "Gel electrophoresis of proteins: a practical approach" Edited by B D Hames and D Rickwood, IRL Press, 1981.

The top of the gel thus includes a number of wells into which are located samples to be analysed by electrophoresis. When the electric field is applied across the tray, differential migration of different components of the samples occurs, in the direction of the length of the tray. The starting, stopping and speed of the separating process is controllable by the voltage source 104. After the gel has been run for at least a minimum length of time, the different components are separated into bands 110.

The bands 110 may be visible to the naked eye, but are clearly visible when the gel is irradiated by a source of U/V radiation or other suitable light source, via a filter if appropriate. This source forms part of the apparatus of FIG. 3.

Thus, referring to FIG. 3, the illustrated apparatus comprises the gel 10 bearing a two dimensional array of bands produced by electrophoretic separation of sample mixtures applied thereto. The fluorescently labelled bands emit light when stimulated by shorter wavelength light 16 from ultra violet source 18.

The resulting emitted light 20 is detected by a cooled charge coupled device detector system, comprising a CCD 2000 Imaging System produced by Astromed Limited, Cambridge, United Kingdom. In the drawing, the basic Astromed imaging system comprises the items 26, 28, 30 and 32. The light 20 first passes through a filter 22 to select the emitted light against the shorter wavelength excitation light. The transmitted or emitted light is then imaged by a lens 24 onto a cooled solidstate-charge coupled device detector 26 (P8600 series CCD made by EEV Ltd) contained in an environmental enclosure 31 and mounted to the outside of a cold box 28 cooled with liquid nitrogen. Cooling could be effected, instead, by means of a Sterling cycle or other mechanical or electrical cooler. Cooling of the detector 26 is generally effected down to an operating temperature of less than $-25°$ C., preferably between $-40°$ and $-120°$ C., and possibly down as low as about $-160°$ C.

The CCD 26, mounted inside the sealed enclosure and cooled by the cold box 28 to the operating temperature, is connected by fine wires to a connector and hence a cable 30 to a driver electronics module included in the CCD 2000 imaging system. This electronics unit, in accordance with the operating characteristics of the system, generates bias and clock signals necessary to drive the CCD in its slow-scan mode of operation. The electronics unit also processes the output signal from the CCD such in a way as to minimise the overall system read-out noise and to maximise the system dynamic range. The electronics unit includes an analog to digital converter such as the Zeltex ZAD 7400 unit which gives true 16 bit digital output (65536 grey levels).

The driver electronics unit is connected by a data cable to an interface board also included in the CCD 2000 System, which is located inside a host computer 34 and connected directly to the computer input/output bus. The computer 34 may be e.g. an IBM PC/AT with EGA screen and keyboard 36 and operates with a resident operating system such as the AT & T UNIX system marketed by Microport Inc, and an application software suite such as the Astromed Command Language.

The computer 34 may have a variety of peripherals attached to it, as the application demands. These may include a disc drive 38 for floppy or hard disks such as drives manufactured by IBM and supplied with IBM computers, magnetic tape decks such as those made by Cifer Inc. and an image display unit 40 such as that made and marketed by Astromed Ltd.

The software in the computer 34 allows data to be taken, displayed, archived and analysed to give a distribution of detected bands of the gel to be determined, together with the detailed properties of the bands such as position, shape, size, orientation and intensity. The data so obtained is output on to a printer 42 such as the Canon LBP-A2 laser printer or an Epson FX 80 dot matrix printer or archived to disk or magnetic tape for storage or to allow comparison with band distributions obtained for other gels.

EXAMPLE 1

Figure 1:
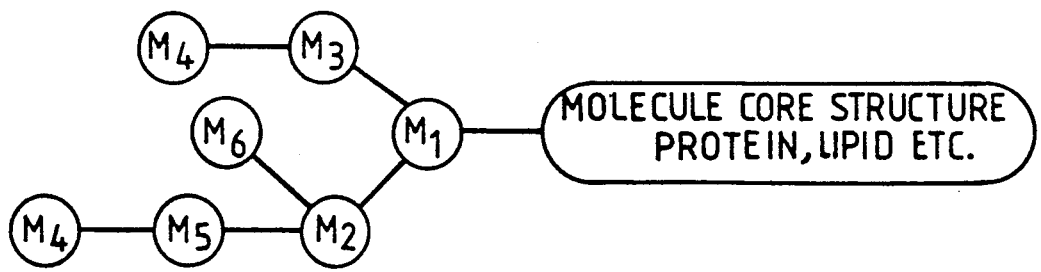
FIG. 1 illustrates a carbohydrate of branched structure.
Figure 4:
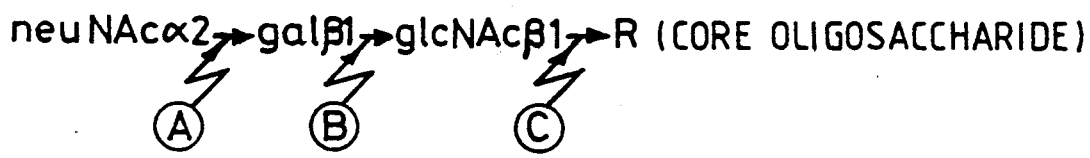
FIG. 4 illustrates a carbohydrate of linear structure.
Figure 5:
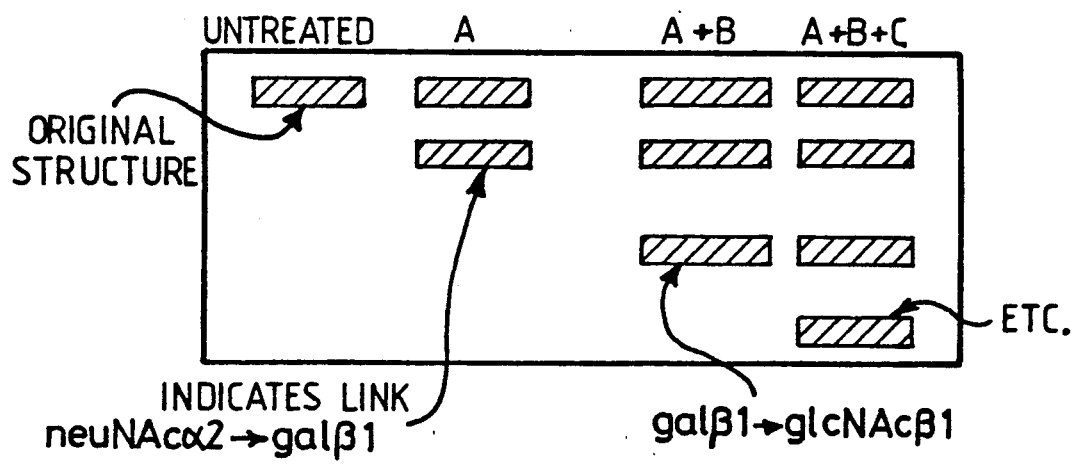
FIG. 5 illustrates a representation of a chromatograph of separated carbohydrate fragments, viewed by a CCD.

Consider the carbohydrate structure illustrated in FIG. 4, which can be cleaved at the points indicated by the arrows using various enzymes (A), (B) and (C), where:

(A)=Neuraminidase (S. Pneumoniae)

(B)=beta-Galactoside (Jack Bean Meal), applied after application of enzyme (A)

(C)=beta-N-acetylglycosaminidase (C. Perfringens), applied after application of enzyme (B).

The original sample is divided into four portions and the first portion left untreated, the second proprotion treated with (A), the third proportion treated with (A)+(B) and the fourth portion treated with (A)+(B)+(C). Each portion will contain different quantities of the four different constituent fragments. The fragments may then be reacted in known manner, for instance involving treatment with sodium periodate or periodic acid, in order to generate reactive aldehydic groups, although such treatment may not be required. The fragments, which may or may not have been treated in this way, may then be derivatised or labelled with a suitable fluorescent reagent such as 9-hydrozinoacridine or amino fluorescein. Each of the four portions is run together on four different tracks of a silica (thin layer chromatography) gel. The resulting gel is illuminated and viewed through a suitable filter by a CCD System, such as the CCD 2000 imaging system described and illustrated above in FIG. 3. The software package associated with the CCD system analyses the resulting image and is able to provide a modified image showing the relative image and intensity of the bands. The resulting image is represented in schematically FIG. 4.

The CCD is capable of viewing many tracks simultaneously. By using various combinations and permutations of different enzymes in as many as forty different tracks, the resulting patterns and information derivable therefrom can enable analysis of complex carbohydrate structures including branched structures.

EXAMPLE 2

As a simple illustration of the principle of the invention, using the preferred gel electrophoresis separation technique, experiments were carried out with the following seven sugars:

| | |
|---|---|
| 1. alpha-L(-) fucose | (a monosaccharide) |
| 2. D(+) glucose | (a monosaccharide) |
| 3. alpha-lactose | (a disaccharide) |
| 4. maltotriose | (a trisaccharide) |
| 5. maltotretraose | (a tetrasaccharide) |
| 6. maltotheptaose | (a heptasaccharide) |
| 7. N-acetylneuramin-lactose | (a trisaccharide) |

Aqueous solutions of the sugars were treated separately with the enzymes neuraminidase and maltase (alpha-glucosidase from Baker's yeast), labelled with the fluoresecent marker aminofluorescein isomer 1, using the technique generally as described in the paper by Prakash et al, and then run on a polycrylamide electrophoretic gel.

0.1 molar aqueous solutions of sugars 1 to 6 and 0.02 molar aqueous solution of sugar 7 were prepared. Two identical 5 ul samples of each of the solutions were placed in test tubes. The first set of 7 samples was denoted group A and the second set group B, and the two groups treated differently as follows.

For group A, to each sample was added the following:

2 ul 0.1 molar sodium acetate buffer pH 5.0 (at 37° C.)

2 ul neuraminidase solution (Sigma type X, from Clostridium perfringens) which contained 0.01 manufacturers units/ul (i.e. 0.02 units).

For group B, to each sample was added the following:

2 ul 0.1 molar sodium phosphate buffer pH 7.5 (at room temperature) containing 10 millimolar 2-mercaptoethanol and 1 millimolar ethylenediamintetraacetic acid disodium salt (EDTA)

2 ul maltase solution (Sigma) (also known as alpha glucosidase; (EC 3.2.1.20) which contained 0.2 manufacturers units/ul.

All the samples in both groups were incubated at 37° C. for 3 hours. Then was added to each sample, in order, 3 ul of glacial acetic acid in solution in water (1 vol acetic acid to 50 vols water)

5 ul 0.2 molar sodium cyanoborohydride in water (freshly made)

10 ul aminofluorescein isomer 1, 0.02 molar in ethanol.

The rectants were mixed, and all the samples incubated at room temperature (about 22° C.) in the dark overnight (about 16 hours).

All the sample-containing tubes were then dried under vacuum in a centrifugal concentrator for 1 hour.

To each tube was then added 25 ul of sample buffer made up as follows:

0.5 ml 2.5 molar Tris-HCl buffer, pH 6.8
3.6 g urea
trace bromophenol blue (marker dye)
water, to make up volume to 10 ml The sample buffer has a final concentration of 0.125 molar Tris-HCl buffer and 6 molar urea.

The reaction products in the sample tubes dissolve on addition of the sample buffer.

Two polyacrylamide electrophoresis gels (gel 1 for samples in group A and gel 2 for samples in group B), each gel having 12 tracks, were prepared and run generally as described in connection with Table 2 on page 134 of the paper by West et al. in Electrophoresis, 1984, 5, 133–138. The gels were about 0.5 mm thick; each separating/resolving gel was about 6 cm long, with a stacking gel about 2 cm long on top.

2.5 ul (except where stated otherwise) of material was loaded per track, as follows:

| Gel 1 | |
|---|---|
| Track | Sample |
| 13 | sample buffer only (5 ul) |
| 14 | water + Flam 1 |
| 15 | alpha-L(-) fucose + Flam 1 |
| 16 | D(+) glucose + Flam 1 |
| 17 | alpha-lactose + Flam 1 |
| 18 | maltotriose + Flam 1 |
| 19 | maltotetraose + Flam 1 |
| 20 | maltoheptaose + Flam 1 |
| 21 | N-acetylneuramin-lactose + Flam 1 |
| 22 | sample buffer only (5 ul) |
| 23 | Flam 1 (no reaction) (1 ul of mixture of 10 ul 0.2 molar Flam 1 in ethanol plus 100 ul sample buffer) |
| 24 | sample buffer only (5 ul) |

Flam 1 = aminofluorescein isomer 1

| Gel 2 | |
|---|---|
| Track | Sample |
| 1 | sample buffer only (5 ul) |
| 2 | water + Flam 1 |
| 3 | alpha-L(-) fucose + Flam 1 |
| 4 | D(+) glucose + Flam 1 |
| 5 | alpha-lactose + Flam 1 |
| 6 | Maltotriose + Flam 1 |
| 7 | Maltotetraose + Flam 1 |
| 8 | Maltoheptaose + Flam 1 |
| 9 | N-acetylneuramin-lactose + Flam 1 |
| 10 | sample buffer only (5 ul) |
| 11 | Flam 1 (no reaction) (1 ul of mixture of 10 ul 0.2 molar Flam 1 in ethanol plus 100 ul sample buffer) |
| 12 | sample buffer only (5 ul) |

The two gels were then run as follows:

at 20 milliamps constant current for approximately 1 hour, at 500 volts constant voltage for approximately 3 hours, at 1000 volts constant voltage for approximately 1 hour, with cooling by a circulating cooling buffer at about +5° C.

After running of the gels, the marker dye bromophenol blue had moved to a position approximately 0.4 along the length of the resolving gel.

The pattern of bands on the gels were visible with the naked eye, in both wet and dry condition, and when illuminated with UV light gave very good results. Significantly better results were obtained viewing the gels with the CCD 2000 imaging system described above, with use of a suitable filter to produce light of a wavelength to which the CCD is sensitive.

Figure 6:
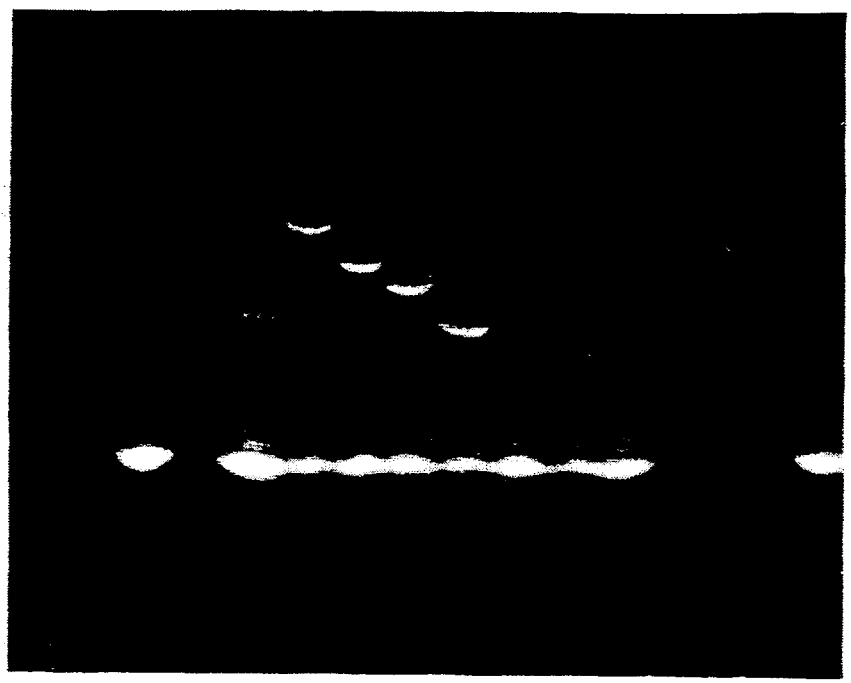
FIG. 6 is a photograph of gel 1 viewed with U.V. light.
Figure 7:
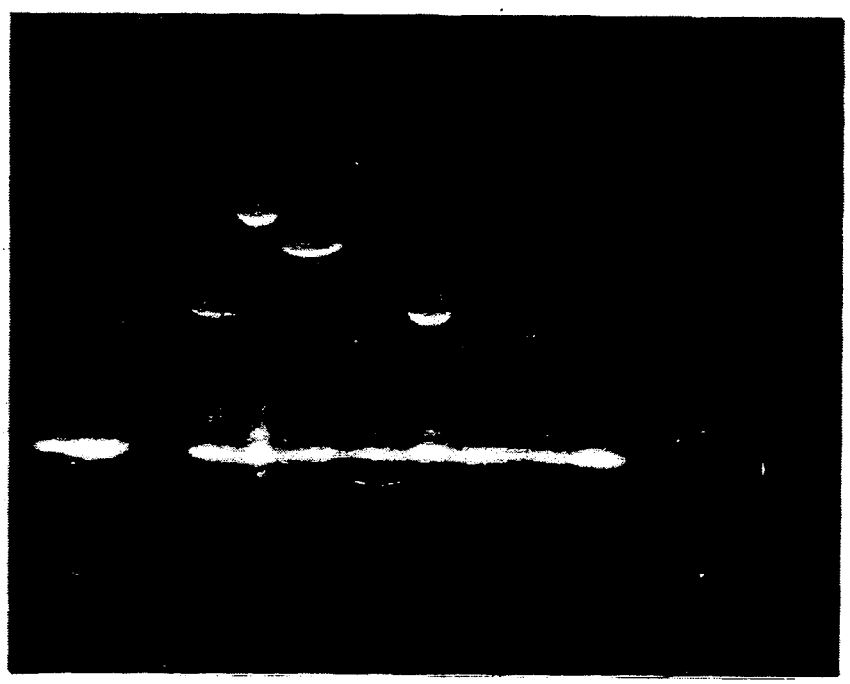
FIG. 7 is a photograph of gel 2 viewed with U.V. light.

FIGS. 6 and 7 are photographs of gels 1 and 2, respectively, viewed with UV light.

Comparison of gel 1 with previously run gels (not shown) shows that the neuraminidase has no effect, so this gel functions as a control. Comparising with gel 2 (maltase treatment) with gel 1 (control) there is a significant change in gel 2 track 6 compared with gel 1 track 18, indicating cleavage of maltotriose by maltase. A slight change in gel 2 track 7 compared with gel 1 track 19 is also apparent, indicating reaction of maltotetraose with maltase.

It is clear that by applying similar treatment to sugars of unknown composition and determining the results of reaction with various different enzymes, information can be obtained about the structure of the unknown sugar. Instead of separating by gel electrophoresis, good results have also been obtained using other techniques, e.g. TLC, in conjunction with imaging with a CCD.

We claim:

1. A method of distinguishing carbohydrate units, comprising labelling the carbohydrate units by reacting a fluorescent label material with a reducing end group of each carbohydrate unit, applying the labelled carbohydrate units to an electrophoretic gel, and running the gel to cause differential migration of different units.

2. A method according to claim 1, wherein the gel comprises a polyacrylamide gel, having a concentration in the range 15% to 60%.

3. A method according to claim 2, wherein the gel has a concentration in the range 25% to 40%.

4. A method according to claim 2, wherein the gel is cross linked.

5. A method according to claim 1, wherein the gel is a gradient gel.

6. A method according to claim 1, wherein the gel is run using a stacking buffer system.

7. A method according to claim 1, wherein light from the gel is viewed using a CCD.

8. A method according to claim 7, wherein light is viewed using a cooled 2-D CCD, operating in slow scan readout.

9. A method according to claim 8, wherein the CCD is cooled to a temperature in the range −25° C. to −160° C.

10. A method according to claim 9, wherein the CCD is cooled to a temperature in the range −40° C. to −120° C.

11. A method according to claim 7, wherein the gel is viewed with the CCD during running of the gel.

12. A method according to claim 1, wherein the carbohydrate units are obtained by decomposing a carbohydrate structure into various constituent fragments.

13. A method of distinguishing carbohydrate units, comprising labelling the carbohydrate units by reacting a label material with a reducing end group of each carbohydrate unit, applying the labelled carbohydrate unit to an electrophoretic gel comprising polyacrylamide having a concentration in the range 15 to 60%, running the gel to cause differential migration of different units, and viewing light from different units using a cooled 2-D CCD, operating in slow scan readout.

* * * * *